United States Patent
Grainger et al.

(10) Patent No.: US 7,041,311 B2
(45) Date of Patent: May 9, 2006

(54) PREPARATION FOR SALIVA FLOW

(75) Inventors: Brian T. Grainger, Princeton, NJ (US); Derek Richard Farley, Sudbury (GB); Ana Paula Ventura da Costa Lopes, Bedford (GB)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 10/376,660

(22) Filed: Feb. 28, 2003

(65) Prior Publication Data

US 2004/0170576 A1    Sep. 2, 2004

(51) Int. Cl.
*A61K 9/68* (2006.01)
*A61K 47/00* (2006.01)

(52) U.S. Cl. .................. 424/439; 424/440; 424/441

(58) Field of Classification Search ................ 424/400, 424/401, 439, 440, 441, 464, 484, 489, 48, 424/49
See application file for complete search history.

(56) References Cited

U.S. PATENT DOCUMENTS

| | | |
|---|---|---|
| 3,885,028 A | 5/1975 | Cella et al. |
| 3,929,987 A | 12/1975 | Colodney et al. |
| 3,980,767 A | 9/1976 | Chown et al. |
| 4,088,788 A | 5/1978 | Ream |
| 4,151,270 A * | 4/1979 | Ream et al. .................. 424/48 |
| 4,479,969 A | 10/1984 | Bakal et al. |
| 4,568,537 A | 2/1986 | Hoerman et al. |
| 4,713,243 A | 12/1987 | Schiraldi et al. |
| 4,820,506 A | 4/1989 | Kleinberg et al. |
| 4,906,455 A | 3/1990 | Hoerman et al. |
| 4,963,369 A | 10/1990 | Song et al. |
| 4,980,169 A | 12/1990 | Oppenheimer et al. |
| 4,983,378 A * | 1/1991 | Parnell .................. 424/48 |
| 4,997,654 A | 3/1991 | Corsello et al. |
| 5,057,328 A | 10/1991 | Cherukuri et al. |
| 5,266,335 A | 11/1993 | Cherukuri et al. |
| 5,354,551 A | 10/1994 | Schmidt |
| 5,496,558 A * | 3/1996 | Napolitano et al. ......... 424/435 |
| 5,834,002 A | 11/1998 | Athanikar |
| 5,843,471 A | 12/1998 | Chaykin |
| 6,177,096 B1 | 1/2001 | Zerbe et al. |
| 6,200,551 B1 * | 3/2001 | Morgan .................. 424/53 |
| 6,306,370 B1 | 10/2001 | Jensen et al. |
| 6,419,902 B1 | 7/2002 | Wright |
| 6,419,903 B1 | 7/2002 | Xu et al. |
| 6,485,710 B1 | 11/2002 | Zuckerman |
| 6,500,409 B1 | 12/2002 | Scherl et al. |
| 6,506,366 B1 | 1/2003 | Leinen et al. |
| 6,537,595 B1 | 3/2003 | Hyodo et al. |
| 2003/0035841 A1 | 2/2003 | Dzijia et al. |

FOREIGN PATENT DOCUMENTS

| | | |
|---|---|---|
| EP | 0 413 427 | 2/1991 |
| EP | 0413427 A2 * | 2/1991 |
| EP | 0 446 170 | 9/1991 |
| EP | 0446170 A2 * | 9/1991 |
| EP | 0 396 634 B1 * | 1/1993 |
| GB | 615323 | 1/1949 |
| WO | 00/18365 | 4/2000 |
| WO | WO 02/47489 | 6/2002 |
| WO | WO 0247489 A1 * | 6/2002 |

* cited by examiner

*Primary Examiner*—S. Tran
(74) *Attorney, Agent, or Firm*—Joseph F. Leightner

(57) ABSTRACT

The present invention is directed to products that promote saliva generation in the mouth through the use of various food grade acceptable acids. The products that enhance saliva production are preferably foods that are consumed in the mouth over a period of time of a minute or longer such as chewing gums, breath films, toothpaste and lozenges.

1 Claim, No Drawings

PREPARATION FOR SALIVA FLOW

FIELD OF THE INVENTION

The present invention is directed to a product, preferably a chewing gum or lozenge that alleviates dry mouth. The product contains a selection of acids, including dibasic acids that have been discovered to overcome dry mouth problems.

BACKGROUND OF THE INVENTION

There have been several disclosures to remedy xerostomia, or dry mouth in the literature. U.S. Pat. No. 4,568,537 discloses a sugarless gum which contains a relatively insoluble, hydrophobic acid, preferably adipic acid. The patent discloses that the acid is released over a 20 to 30 time period that enhances the salivary flow rate into the mouth.

U.S. Pat. No. 4,820,506 discloses the use of from 2 to 3 weight percent organic acid, a sweetener and a saturated calcium phosphate solution. U.S. Pat. No. 4,997,654 discloses the use of from about 4 to 70 weight percent xylitol as a method for treating xerostomia. U.S. Pat. No. 4,983,378 discloses compositions that contain Yerba Santa extract and sweetener that may be formulated in a gum or lozenge form to treat dry mouth.

Despite the disclosures of the prior art there is an ongoing need for the products that treat xerostomia, preferably in an easy to use form such as a gum or lozenge.

SUMMARY OF THE INVENTION

The present invention is directed to compositions and methods for treating dry mouth, xerostomia. One embodiment of the invention comprises a food grade composition containing a flavor package comprising at least about 8 weight percent acid or acid salts selected from the group consisting of citric, malic, adipic, tartaric, glutaric, succinic, and fumaric acids; wherein the food grade composition spends at least one minute in the mouth, also known as xerostomia. A method for treating dry mouth is also disclosed.

DETAILED DESCRIPTION OF THE INVENTION

The acids suitable for use in the present invention include but are not limited to citric, malic, adipic, tartaric, glutaric, succinic and fumaric acids. Those with skill in the art will also appreciate that the food grade acceptable salts of these acids can be used in the present invention. In a preferred embodiment of the invention the acids include the use of acid salts in combination with acids.

The total level of acid and acid salts used in the flavor package of the present invention is greater than about 8 weight percent of the flavor package. One embodiment of the present invention is to only employ acid salts without the inclusion of any intentionally added acids in the flavor package. In a preferred embodiment of the invention we have found that the weight ratio of acid to acid salt ranges from about 0.5 to 2; from about 2 to about 0.5, with a highly preferred embodiment with the weight ratio of acid salts to acid in the flavoring being about 1:1.

The acid level ranges from about 5 to about 15 weight percent of the flavor package, preferably from about 7 to about 12 and most preferably from about 8 to about 10 weight percent of the flavor package. In a highly preferred embodiment of the invention we have discovered that the use of citric acid, malic acid, succinic acid and tartaric acid used in substantially equal amounts of from about 1.5 to about 2.5 weight percent provides extremely advantageous relief of dry mouth, particularly when each of the above acids are employed at about 2 weight percent of the flavor package.

The flavor package also preferably contains disodium succinate and sodium citrate at levels of from about 5 to about 20 weight percent of the flavor package, preferably from about 7 to 15 and more preferably from about 9 to about 12 weight percent of the flavoring system.

The total level of acid and acid salt in the product is from about 0.2 to about 3 weight percent of the total product and preferably from about 0.4 to about 1.5 weight percent of the total product, such as the chewing gum or lozenge.

In another highly preferred embodiment of the present invention the acid and acid salts of the present invention are used in combination with flavoring agents derived from essential oils of peppermint, spearmint, anise, citrus or synthetic flavors of these. In addition other preferred flavor materials include 1-p-menthen-8-thiol and p-mentha-8-thiol-3-one. The level of the flavor materials can vary widely in the flavor package from about 0.3 to about 3.0 weight percent. As those with skill in the art appreciate some flavor materials, such as sulfur containing materials are used in the parts per billion level in flavoring articles.

The remainder of the composition is comprised of sugars, sweeteners, bases, buffers, antioxidants, water, suitable solvents, surfactants, emulsifiers and the like.

The acids and acid salts of the present invention are preferably incorporated in a confectionery product, a lozenge, cough drop or a chewing gum product. These products are well known to those in the art. For example, U.S. Pat. Nos. 4,568,537 and 4,906,455 herein incorporated by reference, disclose chewing gums that treat xerostomia and increase saliva flow. U.S. Pat. No. 4,997,654, also incorporated by reference discloses chewing gum or candy that treat xerostomia through the use of xylitol.

Methods of making cough drops and for enhancing the flavor of these items is disclosed in U.S. Pat. No. 4,980,169 hereby incorporated by reference. A general discussion of the composition and preparation of hard confections, such as cough drops and lozenges may be found in H. A. Liberman, Pharmaceutical Dosage Forms: Tablets, Volume 1(1980); Marcel Dekker Inc., N.Y., N.Y. at pages 339–469.

The manufacture of toothpaste, oral cleaning and dentifrice is also very well known in the art. The literature is complete with descriptions of how to make these products. Examples of these disclosures include U.S. Pat. Nos. 3,885,028; 3,929,987; 3,980,767; 6,306,370; 6,419,902; 6,485,710; 6,500,409 and 6,506,366 hereby incorporated by reference.

Breath films are the now popular confectionery products that frequently are created to dissolve quickly in the mouth, particularly on the tongue. Breath films resemble small pieces of tape, some are substantially transparent that usually placed on the tongue and dissolve rapidly. Even when the breath film dissolves quickly, the flavor system, and more specifically the acids and acid salts of the invention remain in the mouth providing the desired saliva increase. Examples of breath films in the literature include PCT 2000/18365 and U.S. Pat. Nos. 4,713,243; 5,354,551; 6,177,096 and 6,419,903 and U.S. Patent Application U.S. 2002/0035841, the contents of the US Patents and US Application are incorporated by reference.

In a preferred embodiment the flavor package of the present invention is incorporated in a chewing gum composition. These products are preferred because the consumer routinely holds them in the oral cavity, or mouth, for a period of time either chewing or sucking on the product before either swallowing the item or discarding it. For the present invention to create the desired saliva effects in the oral cavity, it is desirable for the item to be in the oral cavity for more than 1 minute, preferably for more than 2 minutes. In highly preferred situations such as occurs with chewing gum, the gum can be chewed for 5 minutes or longer before being swallowed or discarded.

The above description is meant to illustrate the present invention. Those with skill in the art will be able to make various modifications and changes to the invention without departing from the spirit of the invention as set forth herein and as described in the pending claims.

EXAMPLE 1

Thirty-seven volunteers (17 males and 20 females) between the ages of 23 and 50 took part in a test to determine the amount of saliva produced from chewing gum with a flavor package of the present invention.

The volunteers were instructed to chew a piece of gum for a period of about 5 minutes. The volunteers were instructed not to swallow, but rather to expectorate into a pre-weighed cup. The test was repeated.

One piece of gum was a control, not containing the acids or acid salts of the present invention. The other piece of gum contained saliva-producing acids of the present invention containing about 0.75 grams of the acids and acid salts. The volunteers were not told which piece contained the saliva-producing formulation of the present invention. The results are presented in Table 1 below. Control pieces of gum did not contain any of the acids or acid salts. The mouthwatering gum pieces contained the acids and acid salts at 0.7 weight %.

TABLE 1

| Participant | Control | With Mouthwatering | Differences (Mouthwatering-Control) |
|---|---|---|---|
| 1 | 7.14 | 9.4 | 2.26 |
| 2 | 11.3 | 11.74 | 0.44 |
| 3 | 7.55 | 10.69 | 3.14 |
| 4 | 10.5 | 12.62 | 2.12 |
| 5 | 14.33 | 12.9 | -1.43 |
| 6 | 7.69 | 6.58 | -1.11 |
| 7 | 13.09 | 13.57 | 0.48 |
| 8 | 9.36 | 10.26 | 0.9 |
| 9 | 3.1 | 8.29 | 5.19 |
| 10 | 8.48 | 16.52 | 8.04 |
| 11 | 5.05 | 6.61 | 1.56 |
| 12 | 8.16 | 11.07 | 2.91 |
| 13 | 5.71 | 7.61 | 1.9 |
| 14 | 18.79 | 19.9 | 1.11 |
| 15 | 7.72 | 9.25 | 1.53 |
| 16 | 14.93 | 19.94 | 5.01 |
| 17 | 2.12 | 4.66 | 2.54 |
| 18 | 9.39 | 8.28 | -1.11 |
| 19 | 9.93 | 10.61 | 0.68 |
| 20 | 8.09 | 8.79 | 0.7 |
| 21 | 22.24 | 21.86 | -0.38 |
| 22 | 8.14 | 8.2 | 0.06 |
| 23 | 9.57 | 12.15 | 2.58 |
| 24 | 10.89 | 13.8 | 2.91 |
| 25 | 9.88 | 11.58 | 1.7 |
| 26 | 4.62 | 3.53 | -1.09 |
| 27 | 10.01 | 7.36 | -2.65 |
| 28 | 6.1 | 5.34 | -0.76 |

TABLE 1-continued

| Participant | Control | With Mouthwatering | Differences (Mouthwatering-Control) |
|---|---|---|---|
| 29 | 8.06 | 9.43 | 1.37 |
| 30 | 5.26 | 5.6 | 0.34 |
| 31 | 3.99 | 5.85 | 1.86 |
| 32 | 8.09 | 9.82 | 1.73 |
| 33 | 10.61 | 13.43 | 2.82 |
| 34 | 6.86 | 7.26 | 0.4 |
| 35 | 16.13 | 16.9 | 0.77 |
| 36 | 8.82 | 9.83 | 1.01 |
| 37 | 8.18 | 6 | -2.18 |

The saliva producing formulation contained the following flavor recipe (all ingredients reported in weight percent):

| | |
|---|---|
| water | 65 |
| ethanol | 15 |
| disodium succinate | 10 |
| citric acid | 2 |
| malic acid | 2 |
| succinic acid | 2 |
| tartaric acid | 2 |
| sodium citrate | 1 |
| lemon flavor | 0.01 |
| grapefruit flavor | 0.001 |
| rounded to | 100 |

The results of the study indicated that the saliva enhancing formulation when used at a level of 0.7 in the chewing gum produced more saliva in 78% of the volunteers. This result is statistically significant with a 95% confidence level in the amount of saliva produced.

Further questionnaires answered by the volunteers indicated that the saliva enhancing formulation did not have an adverse affect on the perceived sweetness or overall flavor perception of the chewing gum.

What is claimed is:

1. A chewing gum consisting of:
   a gum base; sweetener, buffer, antioxidant, water, emulsifier; and
   a flavor package employed at a level of 0.7 weight percent in the gum, the flavor package consisting of the following ingredients at the weight percent levels

| | |
|---|---|
| water | 65 |
| ethanol | 15 |
| disodium succinate | 10 |
| citric acid | 2 |
| malic acid | 2 |
| succinic acid | 2 |
| tartaric acid | 2 |
| sodium citrate | 1 |
| lemon flavor | 0.01 |
| grapefruit flavor | 0.001; | wherein said acid and acid salts content in the gum weighs about 0.75 grams.

* * * * *